United States Patent [19]

Muto

[11] Patent Number: 5,383,569
[45] Date of Patent: Jan. 24, 1995

[54] AUTOMATIC DELIVERY APPARATUS FOR PREPARED SLIDE GLASS SHEETS

[75] Inventor: Yunosuke Muto, Bunkyo, Japan

[73] Assignee: Muto Pure Chemicals Company Ltd., Tokyo, Japan

[21] Appl. No.: 59,294

[22] Filed: May 11, 1993

[30] Foreign Application Priority Data

May 15, 1992 [JP] Japan ............................. 4-032180[U]

[51] Int. Cl.⁶ ............................................. B65H 3/60
[52] U.S. Cl. ............................ 221/203; 221/259; 271/110
[58] Field of Search .................. 221/259, 277, 43, 239, 221/255, 13, 258, 203, 202, 200, 10, 22; 271/265, 110, 146, 166, 114, 119

[56] References Cited

U.S. PATENT DOCUMENTS

| | | | |
|---|---|---|---|
| 2,896,821 | 7/1959 | Stegeman | 221/259 |
| 3,393,831 | 7/1968 | Stewart | 221/259 |
| 3,583,696 | 6/1971 | Runzi | 271/110 |
| 4,000,821 | 1/1977 | Naito et al. | 221/253 |
| 4,021,032 | 5/1977 | Gross et al. | 271/166 |
| 4,615,169 | 10/1986 | Wurmli | 221/203 |
| 4,653,742 | 3/1987 | Sasaki et al. | 271/114 |
| 4,872,593 | 10/1989 | Behringer | 221/259 |
| 5,127,546 | 7/1992 | Chen | 221/203 |
| 5,150,818 | 9/1992 | DeMoss | 221/255 |
| 5,238,143 | 8/1993 | Crighton | 221/255 |

FOREIGN PATENT DOCUMENTS

| | | |
|---|---|---|
| 2603873 | 3/1988 | France . |
| 9115007.8 | 1/1992 | Germany . |
| 62-012528 | 1/1987 | Japan . |
| 2258459 | 2/1993 | United Kingdom . |

*Primary Examiner*—Kenneth W. Noland
*Attorney, Agent, or Firm*—Oliff & Berridge

[57] ABSTRACT

A container for containing a plurality of glass sheets in a stacked manner has at its bottom an opening through which rollers whose outer peripheries are polygonal and circular in section, respectively, are brought into contact with the undermost glass sheet. The container further has a glass sheet delivery slit with an opening height larger than the thickness of one glass sheet and smaller than the combined thickness of two glass sheets. The rotation of the two rollers causes the glass sheets to be vertically displaced to weaken the adsorptive force between the adjacent glass sheets and to be vibrated to weaken the frictional force between adjacent glass sheets. This results in a frictional force between the two rollers and the undermost glass sheet larger in magnitude than a frictional force between the adjacent glass sheets, which enables the undermost one of the glass sheets being stacked within the container to horizontally displace with the aid of the two rotating rollers. The displacement of the glass sheets other than the undermost glass sheet is restricted by the slit so as to permit only the undermost one to be smoothly transferred in sequence.

7 Claims, 5 Drawing Sheets

AUTOMATIC DELIVERY APPARATUS FOR PREPARED SLIDE GLASS SHEETS

BACKGROUND OF THE INVENTION

1. Field of the Invention

The present invention relates to an apparatus for automatically delivering glass sheets one by one from a stack of a multiplicity of glass sheets for prepared slides.

2. Description of the Related Art

The conventional apparatus of this type comprises a glass sheet container and a feed roller whose outer periphery is circular in section and adapted to come into contact with the undermost one of a plurality of glass sheets being stacked within the container. The glass sheet container includes at its lateral wall a slit having a height larger than the thickness of one glass sheet and smaller than the combined thickness of two glass sheets. The apparatus further comprises a switch which is designed to turn off a motor for driving the feed roller when the glass sheet arrives at the outside of the glass sheet container.

Disadvantageously, the conventional apparatus has involved a problem that the adjacent surfaces of the glass sheets being stacked within the glass sheet container are liable to adhere to each other under the influence of the interfacial function, which may prevent the individual delivery from being smoothly carried out.

SUMMARY OF THE INVENTION

The present invention was conceived in view of the above problem, and the object is to provide an apparatus ensuring a smooth delivery of the glass sheets one by one.

In order to achieve the above object, the apparatus for automatically delivering glass sheets for prepared slides in accordance with the present invention comprises a means for weakening an adsorptive force between the adjacent surfaces of the glass sheets, and a means for imparting to the glass sheet a pressing force larger than the adsorptive force between the adjacent surfaces of the glass sheets so as to ensure a smooth and individual delivery of the glass sheets.

The apparatus for automatically delivering glass sheets for prepared slides according to the first aspect of the present invention comprises a body, and a container which contains a plurality of glass sheets in a stacked manner and has at its bottom an opening, the body including a couple of rollers whose outer peripheries are polygonal and circular in section, respectively, and are each adapted to come into contact with the undermost glass sheet through the opening of the container. The container includes a glass sheet delivery slit having a height larger than the thickness of one glass sheet and smaller than the combined thickness of two glass sheets. When the two rollers rotate, a part of the glass sheets being stacked is vertically vibrated to weaken the adsorptive force between the adjacent ones of the glass sheets being stacked. This results in a frictional Force between the two rollers and the undermost glass sheet larger than a frictional force between the adjacent glass sheets, so that the rotation of the two rollers brings about a horizontal displacement of the undermost one of the glass sheets being stacked within the container. At that time, the glass sheets other than the undermost one are not permitted to be displaced by the presence of the slit, to thereby ensure a smooth and sequential delivery of only the undermost glass sheet to the outside.

On the contrary, the apparatus for automatically delivering glass plates for prepared slides according to the second aspect of the present invention comprises a body and a container which contains a plurality of glass plates in a stacked manner and has at its bottom an opening, the body including a rotational belt having a protrusion which has a height smaller than the thickness of one glass plate to be delivered and is adapted to come into contact with the undermost slide glass through the opening. The container includes a glass plate delivery slit with a height larger than the thickness of one glass plate and smaller than the combined thickness of two glass plates. When the rotational belt rotates, the protrusion is abutted against the edge of the undermost one of the glass plates being stacked within the container. The displacing force of the protrusion causes the undermost glass plate to be horizontally displaced. At that time, the glass plates other than the undermost one are not permitted to be displaced by the presence of the slit to thereby ensure a smooth and sequential delivery of only the undermost glass plate to the outside.

In other words, to this end, the apparatus of the invention comprises a body and a glass sheet container detachably mounted on the body. The glass sheet container includes at its bottom an opening and at its lateral side a slit whose height is larger than the thickness of one glass sheet and smaller than the combined thickness of two glass sheets. The body includes a vibrating roller whose outer periphery is polygonal and a feed roller whose outer periphery is circular, the two rollers being brought into contact with the undermost one of the glass sheets within the container through the opening upon mounting of the glass sheet container onto the body. The body further includes a motor for driving the two rollers, and a switch which is turned off upon the arrival of the glass sheet.

In the case of application to thick glass plates such as mount glasses for prepared slides, the glass sheet transfer means comprises a rotational belt having a protrusion adapted to be abutted against the side edge of the glass plate in lieu of the rollers.

After fitting the glass sheet container into the body, the vibrating roller and feed roller are rotationally driven by the motor. Then the vibrating roller causes the glass sheets within the container to vertically vibrate to weaken the adsorptive force between the adjacent glass sheets. When the frictional force of the feed roller and vibrating roller with respect to the undermost glass sheet becomes larger than the adsorptive forces, the undermost glass sheet being in contact with the rollers is allowed to be transferred through slit provided at the lateral side of the glass sheet container toward the switch of the roller driving motor. The arrival of the leading edge of the glass sheet to the motor causes the switch to turn off to stop the glass sheet. When the glass sheet is removed outside the apparatus, the roller driving motor switch is turned on, and then the above procedures are repeated.

The following description will be made of the rotational belt acting as a glass sheet transfer means and having a protrusion intended to abut against the lateral edge of the glass plate, which is an alternative to the above-described roller. The rotation of the rotational belt with the aid of the drive of the motor causes the protrusion of the rotational belt to abut against the trailing edge of the glass sheet, to thereby impart thereto a pressing force larger than the adsorptive force between the adjacent glass sheets, to urge the glass plate toward the slit.

It is to be appreciated that the glass sheet container to be detachably mounted on the body also functions as a cartridge.

DESCRIPTION OF THE PREFERRED EMBODIMENTS

A first embodiment of the present invention will now be described with reference to FIGS. 1 to 3.

Figure 1:
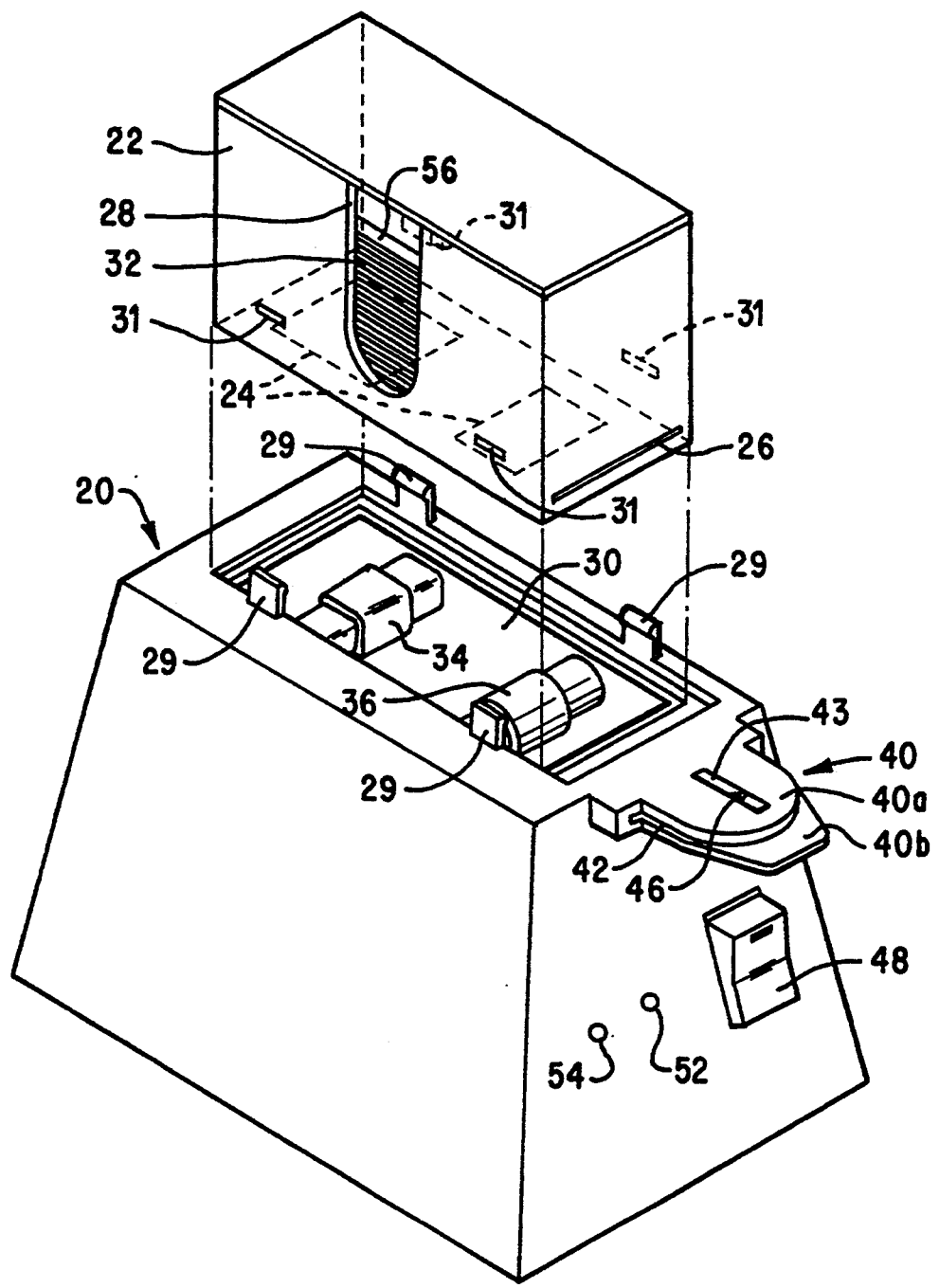
FIG. 1 is a perspective view of a first embodiment constructed in accordance with the present invention.
Figure 2:
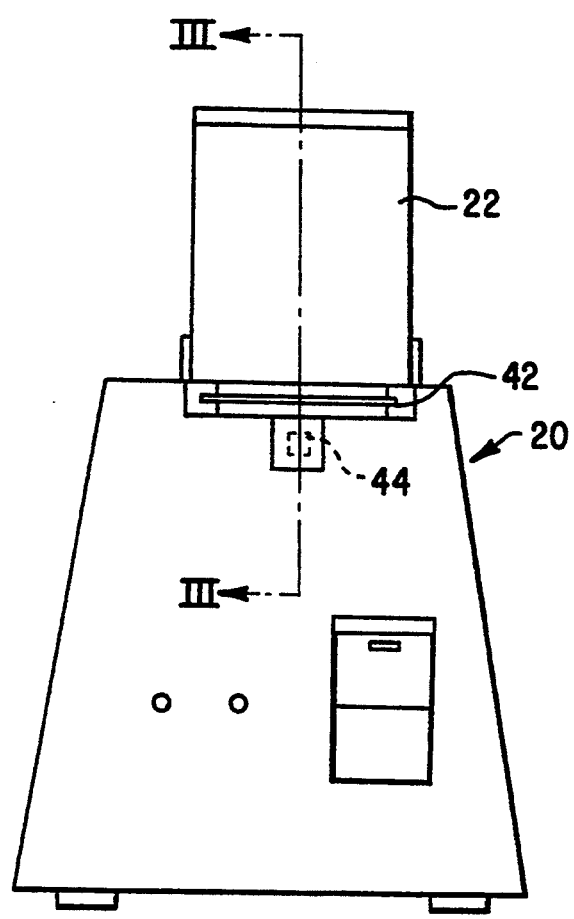
FIG. 2 is a front elevational view thereof.
Figure 3:
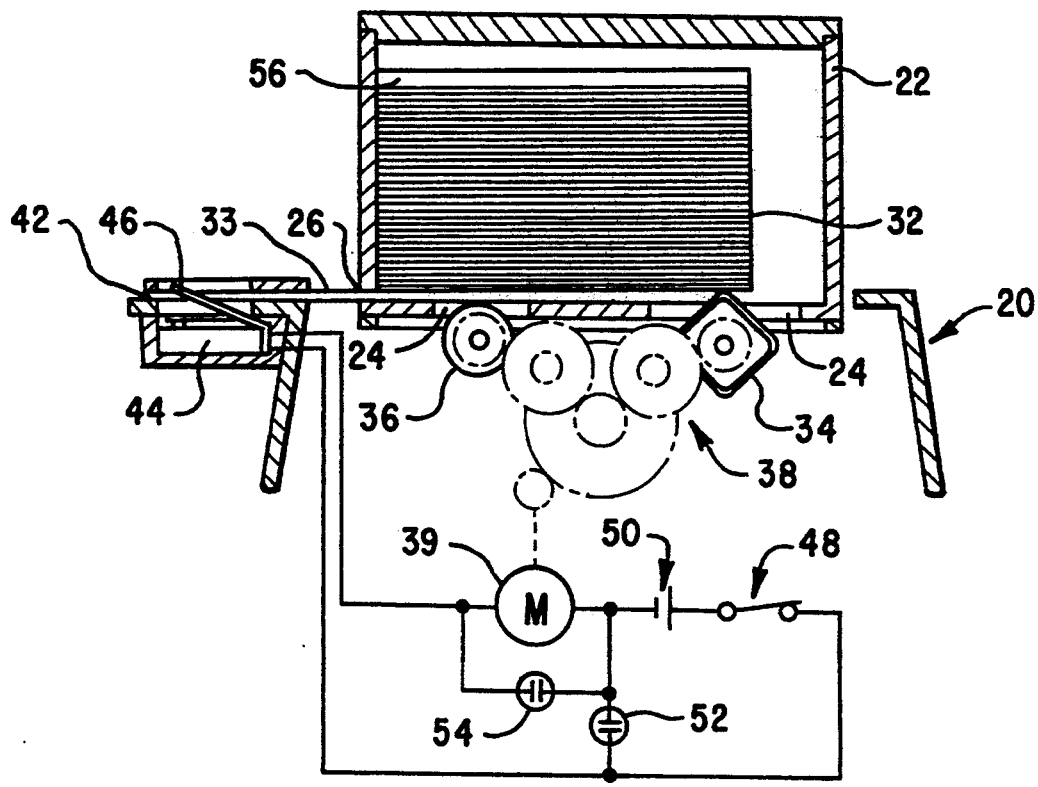
FIG. 3 is a conceptual view depicted by a section taken along a line III—III in FIG. 2 and an associated electrical circuit.

FIGS. 1 through 3 are a perspective view of the first embodiment, a front elevational view of the same, and a conceptual diagram of the apparatus depicted by a section taken along the line III—III in FIG. 2 and an associated electrical circuit, respectively.

It is to be noted in FIG. 3 that the thickness of the glass sheet and the opening height of the through-opening are depicted in enlarged scale than the actual dimensions for better understanding.

A glass sheet container 22 adapted to be detachably mounted on the body generally designated by 20 includes at its underside openings 24, at its front side a slit 26, and at its lateral side a window 28 and a recess 31 for receiving a hook 29. The opening height of the slit 26 is larger than the thickness of one glass sheet 32 and is smaller than the combined thickness of two glass sheets 32 so that a constant frictional force required for the transfer of the glass sheet 32 can be maintained between the glass sheet 32 and the rollers 34 and 36 irrespective of the number of the glass plates remaining.

A typical glass sheet for a prepared slide has a thickness of 0.1 mm to 0.15 mm. In the case of using a glass sheet 0.11 mm thick, a through groove must be of an opening height more than 0.11 mm and less than 0.22 mm. Reference numeral 34 denotes a stimulus roller having in section a rectangular outer periphery, while reference numeral 36 denotes a feed roller having in section a circular outer periphery, each roller including an exterior cladding made of a resilient synthetic resin. The reels 34 and 36 are linked with a shaft of a motor 39 by way of a gear wheel 38 as shown in FIG. 3. A glass sheet unloading portion 40 or a portion through which the glass sheet is removed comprises an upper member 40a and a lower member 40b defining a gap 42 therebetween. The lower member 40b has at its underside a motor switch 44 comprised of a microswitch whose arm 46 extends across the gap 42 into a through groove 43 provided in the upper member 40a.

When a glass sheet container 22 is fitted into a body 20, the stimulus roller 34 and the feed roller 36 are brought into contact with an undermost glass sheet 33, and the gap 42 is aligned with the glass sheet transferred from the container. The motor switch 44 has one terminal connected via a power supply switch 48 to a battery 50 and the other terminal connected via a motor 39 to the battery 50. A power supply on-off pilot lamp 52 and a motor on-off pilot lamp 54 are comprised of LEDs, respectively. Reference numeral 56 designates a weight.

The following is a description of the operation of the first embodiment. When the glass sheet container 22 is fitted into a top opening 30 provided in the body, the undermost plate 33 is allowed to come into contact with both the stimulus roller 34 whose outer periphery is rectangular in section and the feed roller 36 whose outer periphery is circular in section. Upon turning the power supply switch 48 on, the rollers 34 and 36 start to rotate. The rotation of the stimulus roller 34 causes the trailing edge of a stack of glass sheets 32 to vertically vibrate to weaken the adsorptive force arising from an interfacial function between the adjacent glass sheets, thereby facilitating peeling of the undermost plate 33 therefrom. Thus the undermost glass sheet 33 is easily peeled from the other glass sheets by virtue of a frictional force with respect to the feed roller 36 and the stimulus roller 34 and is horizontally transferred. In this manner, the glass sheets are delivered one by one, and the thus delivered undermost glass sheet 33 is transferred by way of a slit 26 into the gap 42. A further advancement of the glass sheets causes a depression of the arm 46 of the microswitch to turn the motor switch 44 off to stop the motor. Thus, the displacement in the weight of the undermost glass sheet 33 activates the motor switch 44. During the transfer of the undermost glass sheet 33, the remaining glass sheets 32 are not allowed to be displaced due to the slit 26 having a smaller height than the combined thickness of the two glass sheets.

Further, each of the glass sheets 32 is pressed against the rollers 34 and 36 due to the force of the weight 56 in such a manner that a constant frictional force required for the transfer of a glass sheet can be kept between the glass sheets 32 and the rollers 34 and 36 irrespective of the number of the glass sheets remaining.

Figure 4:
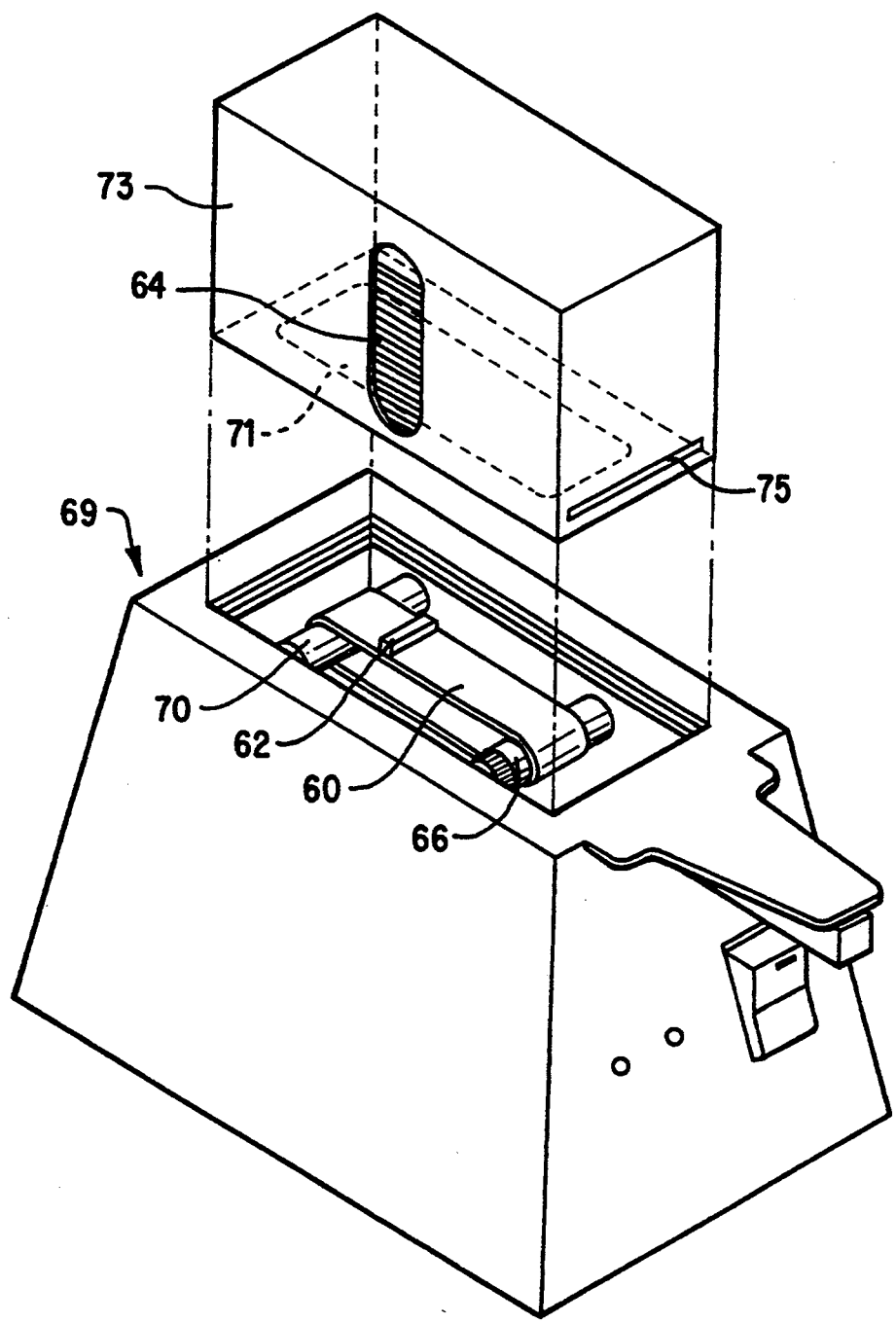
FIG. 4 is a perspective view of a second embodiment constructed in accordance with the present invention.
Figure 5:
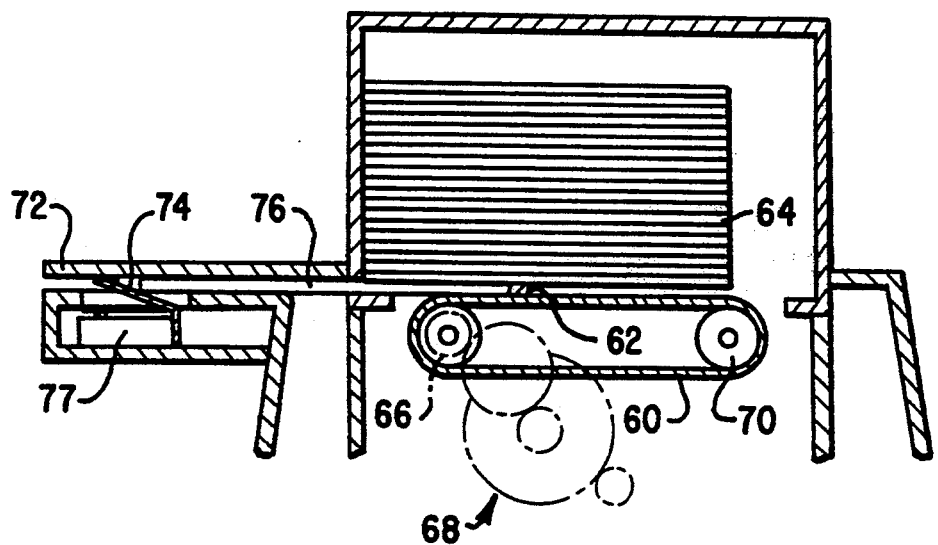
FIG. 5 is a partially sectional view of the second embodiment depicting the portion corresponding to FIG. 3.

A second embodiment of the present invention will next be described with reference to FIGS. 4 and 5. FIG. 4 is a perspective view of the second embodiment, and FIG. 5 is a sectional view depicting the same portion as in FIG. 3.

The description herein is restricted to points different from the first embodiment. A protrusion 62 firmly secured to a rotational belt 60 is intended to push out a glass plate 64 and is configured to have a height slightly less than the thickness of the glass plate 64. A roller 66 which provides a support to the rotational belt 60 is coupled via a gear wheel 68 to a shaft of a motor, not shown. A roller 70 on the other hand is in idle. An upper member 72 of a glass plate unloading portion does not include the groove 43 provided in the first embodiment since the glass plate 64 is of a sufficient thickness for the gap to ensure enough swing of the microswitch arm 74 irrespective of the absence of such a groove.

The following is a description of the operation of the second embodiment. Upon turning the power supply switch on, the rotational belt starts to rotate so that the protrusion 62 securely attached to the belt is pressed against the trailing edge of the undermost glass plate 76. This pressing force causes the undermost glass plate 76 to peel from the other glass plates. Thus the peeled undermost glass plate is horizontally transferred for delivery. The provision of the protrusion 62 on the rotational belt 60 in this manner ensures a delivery of the individual glass plate. As in the first embodiment, the displacement of the remaining glass plates is restricted by the presence of the slit 26. The subsequent operation is the same as the first embodiment. It is to be appreciated that the present invention is not limited to the above embodiments, and that any alteration or modification in design apparent to a person skilled in the art based on these embodiments is included within the scope of the present invention.

The present invention thus constructed presents the following effect.

In an apparatus for automatically delivering glass sheets for prepared slides according to the first aspect of the present invention, the glass sheets are each transferred by means of rollers while being subjected to a vibration, thereby weaken the interfacial adsorptive force between the stacked glass sheets, thus ensuring a smooth delivery of the individual glass sheet to significantly improve the working efficiency.

In an apparatus for automatically delivering glass sheets for prepared slides according to the second aspect of the present invention, there is provided a rotational belt having a protrusion intended for a thick glass plate such as a mount glass, the protrusion being butted against the trailing edge of the glass plate to urge the undermost glass plate by a force overcoming the interfacial adsorptive force between the adjacent glass plates, thus ensuring a smooth delivery of the individual mount glass to significantly improve the operating efficiency.

What is claimed is:

1. A glass sheet delivery apparatus comprising:
   (a) a container for containing a plurality of glass sheets in a stacked manner;
   (b) a polygonal roller having at least three flat sides attached to a bottom of said container for weakening an adsorptive force and a frictional force between adjacent ones of said plurality of glass sheets stacked within said container;
   (c) transfer means for horizontally displacing an undermost one of said plurality of glass sheets stacked within said container;
   (d) restriction means for restricting a horizontal displacement of the glass sheets other than said undermost one;
   wherein
   the rotation of said polygonal roller vertically displaces a part of the plurality of glass sheets to weaken the adsorptive force between the adjacent glass sheets and vibrates the plurality of glass sheets to weaken the frictional force between the adjacent glass sheets so as to ensure a displacement of said undermost glass sheet in the horizontal direction.

2. The glass sheet delivery apparatus according to claim 1, wherein
   said transfer means comprises a circular roller cooperating with said polygonal roller, said rollers each attached to the bottom of said container, and
   said restriction means comprises an opening in said container having a height larger than a thickness of one of said glass sheets and smaller than a combined thickness of two of said glass sheets, wherein after weakening of the adsorptive force and the frictional force between said adjacent glass sheets, said undermost glass sheet is displaced in the horizontal direction by the rotation of said circular roller and said polygonal roller.

3. The glass sheet delivery apparatus according to claim 2, further comprising pressing means for pressing together said plurality of glass sheets being stacked within said container.

4. The glass sheet delivery apparatus according to claim 3, wherein said means comprises a weight disposed on top of said plurality of glass sheets.

5. The glass sheet delivery apparatus according to claim 1, further comprising a switch which acts to simultaneously stop said circular roller and said polygonal roller when said undermost glass sheet is displaced and which acts to simultaneously actuate said circular roller and said polygonal roller when said undermost glass sheet is removed from said container.

6. The glass sheet delivery apparatus according to claim 5, wherein said switch is activated by the displacement of said undermost glass sheet.

7. A glass sheet delivery apparatus according to claim 5, wherein said switch is activated by the weight of said undermost glass sheet.

* * * * *